(12) United States Patent
Reeves

(10) Patent No.: US 6,391,879 B1
(45) Date of Patent: *May 21, 2002

(54) THERAPEUTIC ANTI-FUNGAL NAIL PREPARATION

(75) Inventor: Stanley Forrest Reeves, Demopolis, AL (US)

(73) Assignee: Astan, Inc., Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/640,439

(22) Filed: Aug. 17, 2000

Related U.S. Application Data

(63) Continuation-in-part of application No. 09/193,073, filed on Nov. 16, 1998, now Pat. No. 6,159,977.

(51) Int. Cl.$^7$ .................. A01N 43/58; A01N 43/40; A01N 43/64; A01N 43/50; A01N 47/10

(52) U.S. Cl. .................. 514/252; 514/273; 514/345; 514/359; 514/396; 514/397; 514/497; 514/570; 514/723

(58) Field of Search .................. 514/946, 252, 514/273, 345, 359, 396, 397, 479, 570, 723

(56) References Cited

U.S. PATENT DOCUMENTS

| | | | |
|---|---|---|---|
| 4,073,922 A | | 2/1978 | Wyburn-Mason .......... 424/273 |
| 4,608,249 A | | 8/1986 | Otsuka et al. ............. 424/28 |
| 4,652,557 A | * | 3/1987 | Sandborn ................. 514/164 |
| 4,721,724 A | | 1/1988 | Stettendorf et al. ......... 514/396 |
| 4,927,641 A | | 5/1990 | Knight ..................... 424/665 |
| 5,151,271 A | | 9/1992 | Otsuka et al. ............. 424/443 |
| 5,683,713 A | | 11/1997 | Blank et al. ............... 424/449 |

FOREIGN PATENT DOCUMENTS

| | | | |
|---|---|---|---|
| GB | 2275191 | * | 11/1994 |
| JP | 05148148 | * | 6/1993 |

* cited by examiner

*Primary Examiner*—Alton Pryor
(74) *Attorney, Agent, or Firm*—Kenneth M. Bush; Russell C. Gache'; Sirote & Permutt, P.C.

(57) ABSTRACT

A therapeutic solution and application procedure for curing and preventing nail fungus and athlete's foot infections or Onychomycosis comprising a combination of an anti-fungal agent with DMSO in a anhydrous solution of Polyglycol. The DMSO acts as a solvent so that active anti-fungal agents such as Tolnaftate can be delivered directly to fungal infected areas under and around the nail and other areas prone to topical tinea infections. The DMSO, and Tolnaftate dissolved in a viscous solution of polyglycol so that the combined ingredients may be applied directly to the affected areas with superior penetration. The therapeutic solution is formulated by dissolving the Tolnaftate into the DMSO, and then combining the DMSO and polyglycol solutions together to form the therapeutic solution. Repeated applications of the resulting solution on Onychomycosis infected nails over one 4–6 week period yields satisfactory result rates as high as 85–90% without augmenting the therapy with systemic drugs. Daily applications of the resulting solution on areas vulnerable to tinea infection will prevent and/or delay future episodes. Most versions of the therapeutic solution are anticipated to not require a prescription.

18 Claims, No Drawings

THERAPEUTIC ANTI-FUNGAL NAIL PREPARATION

This application is a continuation-in-part of U.S. Patent application Ser. No. 09/193,073 filed on Nov. 16, 1998, which issued as U.S. Pat. No. 6,159,977, dated Dec. 12, 2000.

FIELD OF THE INVENTION

The present invention relates generally to therapeutic preparations using dimethyl sulfoxide (DMSO) and polyglycol as a transport mechanism to deliver active agents to infected areas. In particular, the present invention relates to therapeutic preparations using DMSO and polyglycol to deliver anti-fungal agents to infected areas that are relatively inaccessible to conventional therapeutic compounds in order to prevent and/or delay future infections.

BACKGROUND OF THE INVENTION

Infections on the exterior of the human body are caused by a variety of micro-organisms, including bacteria, fungi, and molds. Many micro-organisms living on or within the body are beneficial, but others multiply rapidly and may form infections if left untreated. Some organisms such as microscopic plants or fungi can live on the skin and obtain nourishment from dead tissues such as hair, nails, and outer skin layers. When fungi growing on the body grows out of control, an infection can result with detrimental effects to living tissue. In addition, fungal infections are communicable and individuals who frequent swimming pools, gyms, shower rooms, and other humid and/or wet environments are susceptible to being infected with various types of fungal infections as other infected individuals visit these public areas.

One class of external fungi is Onychomrycosis, commonly referred to as nail fungus, Onychomycosis is an infection of the nail (i.e. unguis) and nail bed caused by pathogenic fungi, among other microorganisms, and while not life threatening the disease can cause chronic discomfort and embarrassment. The disease attacks the nails and their growth centers making them appear cracked, yellow, and highly disfigured. In acute cases, Onychomycosis can cause the nail to become thick and yellow in color, making it vulnerable to easy damage and from which subungual hemorrhages can result.

Onychomrycosis is caused by a variety of micro-organisms such as dermatophytes, yeast, and molds. However, the majority of Onychomycosis cases are caused by fungi such as Trichophyton rubrum, Trichophyton mentagrophytes, Trichophyton tonsurans, and Epidermophyton floccosum. Once these microorganisms establish subcutaneous growth, eradication with current over the counter treatment is difficult and recurrences of the disease can be costly and time consuming.

In recent years Onychomycosis has spread to a higher percentage of adults due in part, to its contagious nature and the lack of effective medications that can quickly cure the disease once established within the nail bed. Current treatments include long term (3-9 months) application of topical fungicidal creams and/or solutions in combination with systemic fungal treatment drugs such as griseoflilvin, terbinafine, and itraconazole. Some of the systemic treatments have undesirable side effects such as nausea, headache, photosensitivity, gastrointestinal intolerance, elevated liver enzymes, and undesirable drug interactions, making the process of eradication difficult and troublesome.

It is also noted that systemic fungal treatments are expensive. A treatment program using terbinafine tablets (250 mg) can cost over $600.00 and a therapy using itraconazole can cost between $600.00 and $1,200.00. Conversely, the instant invention contemplates a non-systemic treatment program costing under $50.00.

Part of the difficulty of quickly curing Onychomycosis is the inability to deliver effective anti-fungal agents to the pathogenically active areas such that all of the pathogenic fungus is eradicated. Without full eradication, reoccurrence is likely necessitating a new cycle of combined topical and/or systemic treatments, with the aforementioned systemic effects. Treatment is complicated by the fact that the cutaneous nail shell is not easily penetrated and treatments of infected areas often require thinning of the nail to allow better penetration of anti-fungal agents. The nail acts as a protective barrier under which fungus can grow unhindered and even acts as a vessel for spreading the disease. Current topical anti-fungal ointments and solutions used to treat Onychomycosis do not penetrate in to nail bed easily and tend to leave some portion of the fungus alive after treatment causing reoccurrence of the disease. Heretofore, the medical industry has not produced a topical treatment having the necessary chemical properties to effectively pass through the hard cutaneous nail shell and penetrate into the nail bed for rapid and complete destruction of the fungal infection.

A second class of external fungi is tinea pedis commonly referred to as "athlete's foot." Tinea pedis is the most common infection of all fungal infections. It is also the most persistent. Like onychomycosis, Tinea pedis is caused by dermatophytes such as Trychophyton rubrum, Trychophyton mentagrophytes, Trychophyton tonsurans, and Epidermphyton floccosum. These types of fungi live on the dead tissue of the nails, hair, and outer skin layers. Also like onychomycosis, Tinea Pedis is very contagious, Tinea Pedis thrives in warm, moist areas. Public areas like bathrooms, gyms, and pools are ideals place where tinea pedis can be contacted.

Tinea pedis can be treated with the application of topical anti-fungal medications and with self-care. Tinea pedis can be prevented when certain anti-fungal medications are applied to the areas susceptible to tinea infections. By using anti-fungal medications on a daily basis in a vehicle that can deliver the medication to the site of contact, the majority of tinea pedis cases can be prevented.

Therefore, there is a need for a topical solution that quickly and thoroughly penetrates the nail shell, underlying nail bed, and surrounding nail tissue to deliver an effective anti-fungal agent that will kill the causes of Onychomycosis and Tinea pedis.

SUMMARY OF THE INVENTION

It is the object of the present invention to provide a topical solution containing effective anti-fungal agents that will penetrate the hard cutaneous shell to kill the cause of Onychomycosis.

A further object of the present invention is to provide a method of making the penetrating topical solution.

An even further object of the present invention is to provide for a therapeutic treatment procedure for curing Onychomycosis without the advent of systemic drugs.

In summary, the invention provides for a combination of an anti-fungal agent with the combination of DMSO and an anhydrous solution of polyglycol. The combination of DMSO and polyglycol act as a delivery vehicle so that active anti-fungal agents such as Tolnaftate can be delivered directly to fungal infected areas under and around the nail. The Tolnaftate and DMSO are dissolved in a viscous solution of polyglycol so that the combined ingredients may be applied directly to the affected nails in a topical solution. The therapeutic solution is created by dissolving the Tolnaftate into a portion of the DMSO until dissolution takes place. Then combining the two liquids and adding the balance of the polyglycol until the desired volume is reached. Repeated applications of the resulting solution on Onychomycosis infected nails over a period of 12–16 weeks yields an 85% to 90% satisfactory result rate without augmenting the topical treatments with systemic drugs. Most versions of the preferred solution may be sold over-the-counter and should cost far less than current methods of Onychomycosis eradication.

Another object of the invention is to provide a topical solution containing effective anti-fungal agents that will prevent future episodes of tinea pedis and onychomycosis when used on a daily basis. Daily applications of the resulting solution to areas of skin, nails, and scalp that are susceptible to tinea infections can help prevent and/or delay any future episodes of tinea infections.

Other features and objects and advantages of the present invention will become apparent from a reading of the following description.

DESCRIPTION OF THE PREFERRED EMBODIMENTS

Using DMSO to assist with delivery of chemicals into the blood and tissue is well known. However, use of DMSO to deliver anti-fungal agents through and under nail structure has been heretofore unknown.

In February of 1997, the inventor combined several therapeutic agents with DMSO and conducted experimental trials on human subjects to ascertain the potential for a therapeutic anti-fungal solution and treatment for Onychomycosis. The results were surprising, with satisfactory result rates as high as 85–90% after a twelve (12) week period of treatment, and without systemic drug therapy. In addition, antifungal results were seen as early as two weeks after application in many subjects.

After subsequent experimental trials in which various ingredient concentrations were tried and after further variations in compounding techniques were undertaken, a topical therapeutic solution emerged that has the necessary penetrating characteristics to cure Onychomycosis.

DMS0 (sometimes referred to chemically as $CH_3(SO)$) is a controversial substance having well known solvent properties, as well as being well-known to penetrate human tissue. A wide range of primary pharmacological actions of DMSO have also been documented in laboratory studies such as: membrane transport, anti-inflammation, analgesia, bacteriostasis, non-specific enhancement of resistance to bacteria, vasodilation, muscle relaxation, and reduction in serum cholesterol. While the actual mechanism of penetration enhancement is not precisely known (some studies indicate that increased pedicle flap circulation and histamine liberation are causes), DMSO can act as a carrier of substances into the body for non-ionized molecules of low molecular weight. Studies have also shown that DMS0 increases the permeability of the stratum corneum by increasing its water content.

Some studies indicate that solutions of 90% DMS0 (by volume) are more effective as a transport carrier than solutions using less than or more than 90%. However, clinical trials using experimental versions of the invention show that using a 40% solution of DMSO provides superior absorption and carrier properties for antifungal agents. In particular, the combination of Polyglycol 300 MW (molecular weight) and DMSO (99% purity used at 40% volume) results in an effective carrier for anti-fungal agents such as Tolnaftate, Miconazole and Clotrimazole.

Polyglycol 300 is a viscous, mostly clear solution which is used as an anhydrous base for the invention. Polyglycol 300 is superior as a solution base because it is non-irritating, it has a low order of toxicity in human tissue, it is soluble in most organic solvents, and is clear and non-staining. Furthermore, Polyglycol 300 has viscous properties which allows better retention of the invention on infected areas, such as a nail when applied, thereby improving the dosage volume to infected areas.

Although several types of anti-fungal agents may be used in the instant invention, one agent Tolnaftate USP performs well to kill and prevent both tinea pedis and onychomycosis.

Tolnaftate USP (known by the trade name Tinactin ™) is a white crystalline powder that has been used as a primary agent in anti-fungal preparations. The inventor found that a 1% solution of Tolnaftate is sufficient to kill the fungi in Onychomycosis and tinea pedis and to prevent future occurrences of them when used as directed when used in a penetrating base. Other anti-fungal agents effective in fighting the fungi causing Onychomycosis and tinea pedis and suitable for use in the present invention are: Clotrimazole, Tioconazole, Nystatin, Terconazole, Butoconazole Nitrate, Unecylenic Acid, Clioquinol, Ciclopirox, Olamine, Econazole Nitrate, Triacetin, Miconazole, Flucytosine, and Ketoconazole.

A preferred solution embodying the elements of the invention for producing a 100 ml quantity contains, 40 ml of DMSO, 1 gram of Tolnaftate USP, and 100 ml (q.s.) of polyglycol 300 MW, NF liquid. To compound the preferred solution, measure out (sifting is reconmmended) 1 gram of Tolnaftate. A magnetic stirrer should be employed to facilitate the mixing of ingredients. Measure out 40 ml of DMSO (99% pure). Add the Tolnaftate to the DMSO with stirring and allow all of the powder to dissolve. Add the DMSO/Tolnaftate solution to the polyglycol solution with stirring. Add enough polyglycol to the mixture to bring it to a total volume of 100 ml. Allow the solution to stir for 15 minutes and then remove the stirring plate. The resultant solution will have 40% DMSO and 1% Tolnaftate, by volume in the polyglycol base.

To ensure the strength and the stability of the invention solution, the above procedure should be followed. For example, Tolnaftate is insoluble in some liquids, and hence adding it to DMSO facilitates the dissolution of Tolnaftate more quickly. Using a different mixing procedure may prevent proper dissolution of the ingredient thereby weakening the solution.

In order to kill pathogenic micro-organisms living in an infected nail, a periodic application regime using the preferred solution is required. Nails infected with Onychomycosis should be cleaned and washed, and allowed to dry. The solution is then applied liberally to the infected area and all parts of the nail, including the cuticle. The solution is left to air dry directly onto the infected nail. The application procedure should be repeated 3 times a day for twelve weeks, depending on the severity of the infection. A 12 week application of the invention can yield up to a 85–90% satisfactory result rate in most treatments. Also, the solution can be used against most types of fungi causing Onychomycosis and may be purchased over the counter (according to present Food and Drug Administration guidelines). The applications procedure should be repeated once a day in order to prevent reoccurrence of tinea pedia and onychomycosis.

While I have shown my invention in one form, it will be obvious to those skilled in the art that it is not so limited but it is susceptible of various changes and modifications without departing from the spirit thereof. For example, while the invention teaches a combined solution of DMSO with the anti-fungal agent, it is contemplated that the anti-fungal agent may be combined with polyglycol into a solution which can be applied directly to an affected nail and to which the DMSO may be added directly thereafter. Other such variations embodying the invention are likewise contemplated.

What is claimed is:

1. A topical solution for killing micro-organisms causing ungual fungal infections consisting essentially of:
   (a) an antifungal agent for killing micro-organisms causing said fungal infections;
   (b) a polyglycol base into which said antifungal agent is dissolved; and,
   (c) a solution of DMSO mixed with said polyglycol base;
   (d) wherein said solution is capable of penetrating the unguis to kill the micro-organisms.

2. A topical solution as recited in claim 1, wherein said antifungal agent is selected from the group consisting of Miconazole, Clorrinazole, Tioconazole, Nystatin, Terconazoic, Butoconazole Nitrate, Unecylenic Acid, Clioquinol, Ciclopirox Olamine, Econazole Nitrate, Triacetin, Tolnaftate, Flucytosine, and Ketoconazole.

3. A topical solution as recited in claim 2, wherein said polyglycol has a molecular weight of about 300.

4. A topical solution as recited in claim 1, wherein said topical solution is about 40% volume-DMSO.

5. A topical solution as recited in claim 1 wherein said antifungal agent is between about 1 to about 30% of said solution by volume.

6. A topical solution as recited in claim 1, wherein said antifungal agent is Tolnaftate.

7. A pharmaceutical composition for enhancing penetration of a pharmaceutically active antifungal substance through an unguis and into the surrounding tissue, consisting essentially of:
   (a) an antifungal agent selected from the group consisting of Miconazole, Clotrimazole, Tioconazole, Nystatin, Terconazole, Butoconazole Nitrate, Unecylenic Acid, Clioquinol, Ciciopirox Olamine, Econazole Nitrate, Triacetin, Tolnaftate, Flucytosine, and Ketoconazole;
   (b) a polyglycol base into which said agent is dissolved; and,
   (c) a solution of DMSO mixed with said polyglycol base;
   (d) wherein said composition is capable of penetrating the unguis to kill the micro-organisms.

8. The pharmaceutical composition of claim 7 wherein DMSO is about 40% of the solution volume.

9. The pharmaceutical composition of claim 7 wherein said antifungal agent is from about 1 to about 30% of the solution volume.

10. The pharmaceutical composition of claim 7 wherein said antifungal agent is Tolnaftate.

11. A pharmaceutical composition for enhancing penetration of a therapeutic agent through unguis, consisting essentially of:
   (a) an anti-fungal agent for killing micro-organisms causing fungal infections;
   (b) DMSO used as a solvent for the anti-fungal agent; and
   (c) a polyglycol base into which said anti-fungal agent and DMSO are dissolved;
   (d) wherein said composition is capable of penetrating the unguis to kill the micro-organisms.

12. A composition for enhancing transdermal and transcutaneal penetration of a pharmaceutically active substance, consisting essentially of:
   (a) from about 1 to about 30% by volume of an antifungal agent;
   (b) from about 10 to about 80% by volume of a polyglycol base; and
   (c) from about 10 to about 80% solution of DMSO mixed with said polyglycol base and in an inverse proportion by volume with said polyglycol base;
   (d) wherein said composition is capable of penetrating unguis to kill micro-organisms causing fungal infections.

13. A method of making a therapeutic solution for penetrating unguis to kill micro-organisms causing fungal infections, consisting essentially of the steps of:
   (a) slowly stirring in 1 gram of Tolnaftate into DMSO until dissolved in a first container;
   (b) combining the solution in the first container with polyglycol; and,
   (c) adding additional polyglycol to the combination solution to a desired volume.

14. A method for treating Onychomycosis, comprising:
   (a) applying a solution effective in killing Onychomycosis causing microorganisms to a fungus infected nail, wherein said solution comprises an antifungal agent dissolved in a polyglycol base;
   (b) adding a small quantity of DMSO solution to said Onychomycosis killing solution already applied to said infected nail to enhance penetration of said killing solution through said nail;
   (c) allowing the combination of DMSO and said solution to air dry; and
   (d) repeating steps a–c 3 to 4 times daily for 4–6 weeks.

15. A method of killing micro-organisms causing nail fungal infections, comprising applying a solution effective in penetrating unguis to a human nail, said solution consisting essentially of:
   (a) an anti-fungal agent selected from the group consisting of Miconazole, Clotrimazole, Tioconazole, Nystatin, Terconazole, Butoconazole Nitrate, Unecylenic Acid, Clioquinol, Ciclopirox Olamine, Econazole Nitrate, Triacetin, Tolnaftate, Flucytosine, and Ketoconazole;
   (b) a solution of DMSO; and
   (c) a polyglycol base into which said agent and said DMSO are dissolved.

16. The method of claim 15 wherein said anti-fungal agent is Tolnaftate.

17. The method of claim 15 wherein said anti-fungal agent is from about 1 to, about 30% of the solution volume.

18. The method of claim 15 wherein said DMSO is about 40% of the solution volume.

* * * * *